United States Patent [19]

Brown et al.

[11] Patent Number: 4,797,505

[45] Date of Patent: Jan. 10, 1989

[54] PROCESS FOR THE PREPARATION OF SUBSTITUTED DIPHENYL ETHERS

[75] Inventors: Michael J. Brown, Randolph; Kou-Chang Liu, Wayne, both of N.J.

[73] Assignee: GAF Corporation, Wayne, N.J.

[21] Appl. No.: 358,974

[22] Filed: Mar. 17, 1982

[51] Int. Cl.$^4$ .............................................. C07C 79/46
[52] U.S. Cl. ..................................... 560/021; 558/244; 558/248; 558/251
[58] Field of Search ................... 560/21; 558/248, 244, 558/217

[56] References Cited

FOREIGN PATENT DOCUMENTS 0020052 10/1980 European Pat. Off. .
0034883 2/1981 European Pat. Off. .

*Primary Examiner*—Paul J. Killos
*Attorney, Agent, or Firm*—Marilyn J. Maue; Joshua J. Ward

[57] ABSTRACT

This invention relates to certain phenoxybenzoates having excellent selective herbicidal properties. The compounds of the present invention are defined by the formula

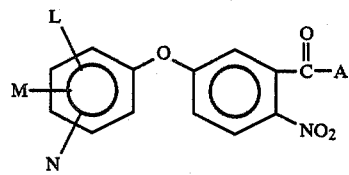

wherein L, M and N are independently hydrogen, halogen, trihalomethyl, nitro, cyano, $C_{1-4}$ alkyl, $C_{1-4}$ alkoxy and

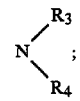

and A is selected from the group of radicals defined by the formulae:

$$-Z(CH_2CH_2Z')_mCH_2CH_2Z''H; \qquad \text{I}$$

$$-XR_5X'\overset{O}{\underset{\|}{C}}(X'')_nR_6; \qquad \text{II}$$

$$-X(CH_2)_nR_6(OH)_p; \qquad \text{III}$$

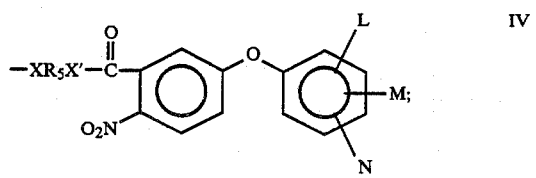

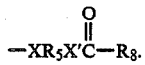

and $$-XR_5X'\overset{O}{\underset{\|}{C}}-R_8. \qquad \text{VI}$$

29 Claims, No Drawings

PROCESS FOR THE PREPARATION OF SUBSTITUTED DIPHENYL ETHERS

The present process provides an efficient and economical method for the synthesis of certain substituted phenyl ethers, having the formula wherein L, M and N are independently hydrogen, halogen, trihalomethyl, nitro, cyano, $C_{1-4}$ alkyl, $C_{1-4}$ alkoxy and $$N\begin{matrix}R_3\\\\R_4\end{matrix};$$

and A is selected from the group of radicals defined by the formulae:

$-Z(CH_2CH_2Z')_mCH_2CH_2Z''H;$      I $-XR_5X'\overset{O}{\overset{\|}{C}}(X'')_nR_6;$     II $-X(CH_2)_nR_6(OH)_p;$     III

IV $-OCH-R-CHOH$
$\quad\ \ |\qquad\ \ \ |$
$\quad\ R_1\qquad\ R_2$     V and $-XR_5X'\overset{O}{\overset{\|}{C}}-R_8$     VI wherein R is an unsaturated, straight chain or branched aliphatic radical having from 2 to 8 carbon atoms;

$R_1$ and $R_2$ are independently hydrogen or alkyl of 1 to 4 carbon atoms;

$R_3$ and $R_4$ are independently hydrogen, or a saturated or unsaturated straight or branched chain $C_{1-8}$ aliphatic radical optionally substituted with halogen, hydroxy, alkoxy, cyano or nitro;

$R_5$ is a saturated or unsaturated, straight chain or branched aliphatic hydrocarbon radical of from 1 to 18 carbon atoms wherein one or more of the $-CH_2-$ groups can be replaced with $-O-$, $-S-$, $-S-S-$, $-SO-$ or $-SO_2-$ and said hydrocarbon radical is optionally substituted with halogen, trihalomethyl, cyano, aryl, hydroxy, alkoxy, nitro or cycloalkyl having 3 to 6 carbon atoms;

$R_6$ is a saturated or unsaturated straight chain or branched aliphatic radical containing from 1 to 8 carbon atoms, optionally substituted with halogen, trihalomethyl, cyano, hydroxy, nitro, acetoxy, alkoxy, thioalkoxy or aryl; an aryl radical optionally substituted with halogen, trihalomethyl, hydroxy, cyano, nitro, alkyl or alkoxy; a cyclic 3–6 membered alkylene ring or a 5–6 membered alkenylene ring or benzyl optionally substituted with halogen, trihalomethyl, alkyl, hydroxy, alkoxy or cyano;

$R_8$ is $-\overset{O}{\overset{\|}{C}}-(O)_nR_6$, $-R_9-\overset{O}{\overset{\|}{C}}-(OR_9)_n(O)_nR_6$ or each $R_9$ is independently an alkylene diradical having from 1 to 4 carbon atoms;

X, X' and X'' are independently $-O-$, $-S-$ or $-NR_4-$;

Z and Z'' are independently, $-O-$ or $-S-$, Z'' additionally can be thiol or $-SO_3-$; and Z' is $-S-$, $-S-S-$, $-SO-$ or $-SO_2-$;

p has a value of 2–6; n in each instance, has a value of 0 or 1; and m has a value of 1–6. The synthesis of these compounds is defined by a 2-, 3- or 4 steps process wherein the first 2 steps involve reacting a substituted phenoxybenzoic acid having the formula

A.

with a diacylating agent having the formula HXA'X'H wherein A' is $R_5$, $-CH-(R)_n-CH-$ or $-(CH_2)_nR_6(OH)_{p-1}$
$\ \ |\qquad\qquad\ \ |$
$\ R_1\qquad\qquad R_2$ at a temperature between about 20° and about 200° C. under from about 1 to about 5 atmospheres pressure for a period of from about 1 to about 40 hours; preferably at a temperature between about 100° and 150° C. under atmospheric pressure for a period of from about 10 to about 40 hours, to produce the corresponding bis-compound having the formula

B.

and then nitrating the bis-compound with a conventional nitrating agent at a temperature between about −5° and about +70° C. under atmospheric pressure for a period of from about 1 to about 10 hours; preferably at a temperature between about 0° C. and about 30° C. for a period of from about 1 to about 5 hours, to produce the corresponding nitrated compound having the formula:

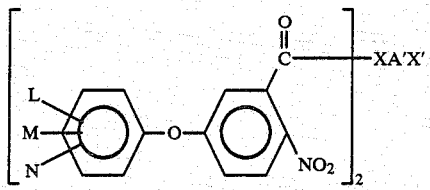

It will be appreciated that when A' is R$_5$, the product of formula 1 A-IV is directly produced by the second step, i.e. nitration step C.

Examples of suitable acylating agents include ethylene glycol, 2-hydroxyethyl ether, 2,2'-thiodiethanol, 1,2-ethanedithiol, ethylenediamine, 2-mercaptoethanol, 1,4-butenediol, 2-hydroxyethyl sulfide, and the like.

The above nitration step can be carried out in the absence or in the presence of an inert solvent, such as methylene dichloride, ethylene dichloride, chloroform, carbon tetrachloride, etc. Suitable nitrating agents include nitric acid/sulfuric acid, potassium nitrate/sulfuric acid, nitric acid/sulfuric acid/acetic anhydride and other conventional nitrating mixtures. When a solvent is employed, the concentration of the bis compound can be varied over a wide range limited only by economic considerations; however, it is found that concentrations between about 10 and about 80 weight percent provides good results.

The mole ratio of diacylating agent to the phenoxybenzoic acid is most preferably about 1:2. The mole ratio of NO$_2$$^+$ in the nitrating agent is most preferably 2:1 with respect to the intermediate bis-compound; although a greater excess of nitrating agent, can be employed if desired.

When compounds of formula 1 having A group I, III and V are desired, the nitrated product of the 2 step process described above is transacylated by reacting it with at least an equimolar amount of an above-described diacylating agent at a temperature of between about 20° and about 250° C. under from about 1 to about 5 atmospheres pressure for a period of 0.5 to about 20 hours; preferably at a temperature between about 140° and about 200° C. under atmospheric pressure for a period of from about 1 to 10 hours. The reaction is generally defined by the equation:

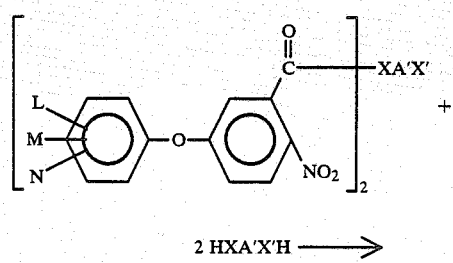

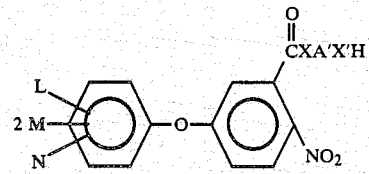

The transacylating step is preferably carried out in a presence of a transacylating catalyst such as sulfuric acid, p-toluene sulfonic acid, hydrogen halide, hydrate manganese acetate, boron trifluoride etherate, phosphoric acid, calcium oxide, barium oxide, lead oxide, sodium oxide, lead nitrate, zinc acetate, manganese borate, zinc borate or an acidic ion exchange resin. Of these transesterification catalysts, manganese acetate tetrahydrate has been found to be very effective. The mole ratio of diacylating agent employed in this third step of the reaction is between about 1:1 and 50:1, preferably between about 3:1 and about 20:1 with respect to the nitrated product of Step C. The excess and unreacted diacylating agent in this stage functions as a solvent for the transacylation reaction and is preferably separated from the product for recycle.

When the 3-step process is carried out in batch operation the various coreactants in each step are added sequentially after substantial completion of the preceding reaction. However, the synthesis may also be effected in separate reactors operated in series with heating and/or cooling devices between the various stages, as required. Also unreacted components may be separated from product and recycled to the appropriate stage.

To obtain the products of A groups II and VI, the product of equation D is reacted with a carbonyl-containing compound of the formula

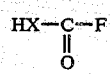

or the acid halide or anhydride of such carbonyl-containing compounds wherein X, X'' and n are as defined above and F is $(X'')_n R_6$ or $R_8$, according to the reaction defined by equation E;

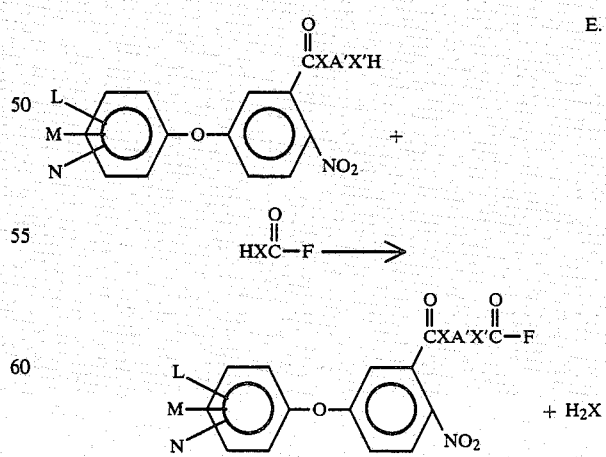

Reaction E is effected at a temperature of between about 0° C. and about 200° C. under a pressure of from atmospheric to about 5 atmospheres over a period of from 0.5 to 20 hours; preferably at between about 25° C.

and about 75° C. under atmospheric pressure over a period of from about 1 to 10 hours.

Suitable carbonylating agents include acetic acid, chloroacetic acid, thioacetic acid, N,N-dimethylcarbamyl chloride, pyruvic acid, propionic acid, methoxyacetyl chloride, acetic anhydride, phthalic anhydride, and the like.

The carbonyl-containing reactant is employed in a mole ratio of from about 1:1 to about 20:1 with respect to the product of reaction D. If desired the carbonylation can be effected in the presence of an inert solvent, e.g. tetrahydrofuran, and any of those previously given for the nitration reaction C. However, this reaction can be effected in the absence of solvent or in the presence of excess carbonyl-containing compound which excess may function as a recyclable solvent to this stage of the reaction.

The product compounds of the present invention are those named in Tables I of co-pending patent applications, Ser. Nos. 239,286 filed Mar. 2, 1981; 266,675 filed May 22, 1981; 283,402 filed July 15, 1981; 292,320 filed Aug. 12, 1981; 301,664 filed Sept. 14, 1981 and 310,663 filed Oct. 13, 1981 which disclosures are incorporated herein by reference. As described in the foregoing applications the present products of this invention are useful as herbicides and may have additional uses and applications depending upon the particular compound.

Having generally described the process of this invention, reference is now had to specific preferred embodiments described in the following examples, in which all amounts and proportions are reported by weight unless otherwise indicated. It is to be understood that the scope of this invention is not to be limited to these examples and is instead defined by the foregoing disclosure and the appended Claims.

EXAMPLE 1

Preparation of 1,2-Bis[5-(2-chloro-4-trifluoromethylphenoxy)-2-nitrobenzoyloxy]ethane A. In a 250 ml glass flask, xylene (100 cc), 3-(2-chloro-4-trifluoromethylphenoxy) benzoic acid (131.6 g., 0.1 mole), ethylene glycol (6.2 g., 0.1 mole) and conc. sulfuric acid (2 g.) were heated to reflux (130° C.) while azeotroping off about 2 cc of a water-glycol mixture. The temperature was maintained for 30 hrs., after which the mixture was cooled to room temperature. The product mixture was then analyzed by thin layer chromatography (10:1 toluene/ethyl acetate on silica) and the following product separations were reported: $R_f=0.71$ (major spot-product), 0.47 (monoester), and 0.13 (starting material). The reaction mixture was partitioned between ethyl acetate and a 5% sodium bicarbonate solution. The organic phase was reduced in volume by evaporation leaving 25.4 g of crude bis-ester, which was subjected to column chromatography eluting with a 3:1 toluene/CH$_2$Cl$_2$ solvent mixture. The product fractions averaged 20.6 g. (62.6%) upon evaporation. Recrystallization from 5:1 hexane/toluene yielded 16.2 g. of 1,2-bis[5-(2-chloro-4-trifluoromethylphenoxy)benzoyloxy]ethane; m.p. 98° C.; nmr (CDCl$_3$); δ 8.1–6.9 (7, m, CH—Ar), 4.7 (4, s, CH$_2$); ir (neat) 1726 cm$^{-1}$ (C=O).

B. A solution of 1,2-bis[5-(2-chloro-4-trifluoromethylphenoxy)benzoyloxy]ethane (6.6 g., 0.01 mole) in 15 cc of dichloroethane was treated with 10.4 g. of ca. 33/67 nitric/sulfuric acid at 2°–4° C. for 1.75 hours. Thin layer chromatography (3:1 toluene/CH$_2$Cl$_2$ on silica) analysis indicated a product with $R_f=0.39$. Water (15 cc) was added dropwise at 0°–5° C. The layers were separated and the organic phase was washed sequentially with 5% sodium bicarbonate and water. The solvent was removed by rotary evaporation leaving 6.3 g. of 1,2-bis[5-(2-chloro-4-trifluoromethylphenoxy)-2-nitrobenzoyloxy]ethane (84%); nmr (CDCl$_3$)δ 8.1–7.0 (10, m, CH—Ar), 4.6 (4, s, CH$_2$); ir (neat) 1750 (C=O), 1530 cm$^{-1}$ (NO$_2$).

Other compounds having the general formula 1 where A is group IV are prepared by the above procedure A. and B. except for substitution of the ethylene glycol reactant in step A.

Accordingly, 1,3-bis[5-(2-chloro-4-trifluoromethylphenoxy)-2-nitrobenzoyloxy]propane is prepared by substituting 1,3-propandiol for ethylene glycol in Step A; 1,5-bis[5-(2-chloro-4-trifluoromethylphenoxy)-2-nitrobenzoyloxy]3-oxapentane is prepared by substituting 2-hydroxyethyl ether for ethylene glycol in Step A; and 1,6-bis[5-(2-chloro-4-trifluoromethylphenoxy)-2-nitrobenzoyloxy]3,4-dithiahexane is prepared by substituting 2-hydroxyethyl disulfide for ethylene glycol in Step A.

EXAMPLE 2

Preparation of [2-Hydroxy ethyl]5-(2-chloro-4-trifluoromethylphenoxy)-2-nitrobenzoate The reaction product of Example 1 B, 1,2-bis[5-(2-chloro-4-trifluoromethylphenoxy)-2-nitrobenzoyloxy]ethane (6.1 g, 0.008 mole) was mixed with ethylene glycol (10.1 g., 0.16 mole) and manganese acetate tetrahydrate (0.4 g.) and heated at 165°–185° C. for 5 hours, and then cooled to room temperature. The product mixture was then subjected to thin layer chromatographic analysis (5:1 toluene/ethyl acetate on a silica gel support); which showed a single spot with $R_f=0.2$ identified as 2-hydroxyethyl 5-(2-chloro-4-trifluoromethylphenoxy)-2-nitrobenzoate. This indicated that complete transacylation had taken place.

The mixture was partitioned between water and toluene/ethyl acetate and the volume of the organic phase was reduced by rotary evaporation. The resulting product was then subjected to high pressure liquid chromatography purification employing a 5:1 toluene/ethyl acetate solvent system. The product fractions (4.2 g, 65%) were identified by Thin Layer Chromatography, nmr and ir. High pressure liquid chromatography analysis revealed a 88.3% purity with a trace of bis-nitro ester and less than 1% 5-[2-chloro-4-trifluoromethylphenoxy]-2-nitrobenzoic acid.

The reaction of this example can be employed to make other nitrobenzoates by proper substitution of 1,2-bis[5-(2-chloro-4-trifluoromethylphenoxy)-2-nitrobenzoyloxy]ethane. For example, [3-hydroxy propyl]5-(2-chloro-4-trifluoromethylphenoxy)-2-nitrobenzoate is prepared by substituting 1,3-bis[5-(2-chloro-4-trifluoromethylphenoxy)-2-nitrobenzoyloxy]propane; [5-hydroxy-3-oxapentyl]5-(2-chloro-4-trifluoromethylpehnoxy)-2-nitrobenzoate is prepared by substituting 1,5 bis[5-(2-chloro-4-trifluoromethylphenoxy)-2-nitrobenzoyloxy]-3-oxapentane; [5-hydroxy-3-thio-pentyl] 5-(2-chloro-4-trifluoromethylphenoxy)-2-nitrobenzoate is prepared by substituting 1,5-bis[5-(2-chloro-4-trifluoromethylphenoxy)-2-nitrobenzoyloxy]-3-thiapentane and [4-hydroxy-2-buten-1-yl]5-(2-chloro-4-trifluoromethylphenoxy)-2-nitrobenzoate is prepared by substituting 1,4-bis[5-(2-chloro-4-trifluoromethyl-phenoxy)-2-nitrobenzoyloxy]-2-butene for 1,2 bis[5-(2-chloro-4-trifluoromethylphenoxy)-2-nitrobenzoyloxy]ethane in this example.

EXAMPLE 3

Preparation of [2-Chloroacetoxyethyl]5-(2 chloro-4-trifluoromethylphenoxy)-2-nitrobenzoate Chloroacetyl chloride (3 g, 0.027 mole) was added dropwise to a stirred solution of [2-hydroxyethyl]5-(2-chloro-4-trifluoromethylphenoxy)-2-nitrobenzoate (8.1 g, 0.02 mole), triethylamine (2.5 g), and ether (150 ml). The heat given off during the reaction raised the temperature of the ether solution to reflux. After completion of addition, the mixture was kept at reflux for 10 min. The mixture then was allowed to cool to room temperature, poured into 200 ml of water, and 400 ml of ether was added. The ether extract was washed three times with water, dried CaSO$_4$ and condentrated to 8.6 g of yellowish oil. The oil was column chromatographed through silica gel with 20% ethyl acetate-80% hexane as eluent to afford 3.2 g of pure [2-chloroacetoxyethyl]5-(2-chloro-4-trifluoromethylphenoxy)-2-nitrobenzoate, as a pale yellow gummy material; nmr (CDCl$_3$) δ 4.16 (S, 2H), 4.50 (S, 4H), 6.98–8.18 (m, 6H); ir (CHCl$_3$) 1752, 1765.

Other carbonylated compounds can be prepared by the procedure of this example by proper substitution of chloroacetyl chloride. Thus, [2-(methoxyacetoxy)ethyl]5-(2-chloro-4-trifluoromethylphenoxy)-2-nitrobenzoate is prepared by substituting methoxyacetyl chloride for chloroacetyl chloride; [2-acetoxyethyl]5-(2-chloro-4-trifluoromethylphenoxy)-nitrobenzoate is prepared by substituting acetic anhydride for chloroacetyl chloride; [2-(propionyloxy)ethyl]5-(2-chloro-4-trifluoromethylphenoxy)-2-nitrobenzoate is prepared by substituting propionyl chloride for chloroacetyl chloride and [2-(N,N-dimethylcarbamyloxy) ethyl]5-(2-chloro-4-trifluoromethylphenoxy)-2-nitrobenzoate is prepared by substituting N,N-dimethylcarbamyl chloride for chloroacetyl chloride.

What is claimed is:

1. The process for the preparation of substituted diphenyl ethers having the formula:

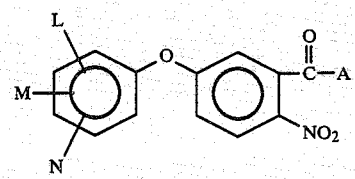

wherein L, M and N are independently hydrogen, halogen, trihalomethyl, nitro, cyano, C$_{1-4}$ alkyl, C$_{1-4}$ alkoxy and

and A is selected from the group of radicals defined by the formulae:

—Z(CH$_2$CH$_2$Z')$_m$CH$_2$CH$_2$Z"H;   I

—XR$_5$X'C(X")$_n$R$_6$;   II

—X(CH$_2$)$_n$R$_6$(OH)$_p$;   III

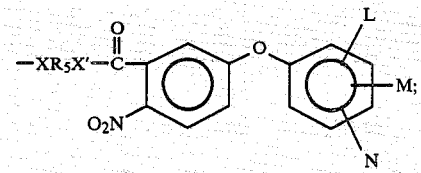

—OCH—R—CHOH   V
   |         |
  R$_1$     R$_2$ and

—XR$_5$X'C(O)—R$_8$   VI wherein

R is an unsaturated, straight chain or branched aliphatic radical having from 2 to 8 carbon atoms;

R$_1$ and R$_2$ are independently hydrogen or alkyl of 1 to 4 carbon atoms;

R$_3$ and R$_4$ are independently hydrogen, or a saturated or unsaturated straight or branched chain C$_{1-8}$ aliphatic radical optionally substituted with halogen, hydroxy, alkoxy, cyano or nitro;

R$_5$ is a saturated or unsaturated, straight chain or branched aliphatic hydrocarbon radical of from 1 to 18 carbon atoms wherein one or more of the —CH$_2$— groups can be replaced with —O—, —S—, —S—S—, —SO— or —SO$_2$— and said hydrocarbon radical is optionally substituted with halogen, trihalomethyl, cyano, aryl, hydroxy, alkoxy, nitro or cycloalkyl having 3 to 6 carbon atoms;

R$_6$ is a saturated or unsaturated straight chain or branched aliphatic radical containing from 1 to 8 carbon atoms, optionally substituted with halogen, trihalomethyl, cyano, hydroxy, nitro, acetoxy, alkoxy, thioalkoxy or aryl; an aryl radical optionally substituted with halogen, trihalomethyl, hydroxy, cyano, nitro, alkyl or alkoxy; a cyclic 3-6 membered alkylene ring or a 5-6 membered alkenylene ring or benzyl optionally substituted with halogen, trihalomethyl, alkyl, hydroxy, alkoxy or cyano;

R$_8$ is —C(O)—(O)$_n$R$_6$, —R$_9$—C(O)—(OR$_9$)$_n$(O)$_n$R$_6$ or

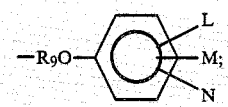

each R$_9$ is independently an alkylene diradical having from 1 to 4 carbon atoms;

X, X' and X" are independently —O—, —S— or —NR$_4$—;

Z and Z" are independently, —O— or —S—, Z" additionally can be thiol or —SO$_3$—; and Z' is —S—, —S—S—, —SO— or —SO$_2$—;

p has a value of 2-6; n in each instance, has a value of 0 or 1; and m has a value of 1-6;

which comprises reacting a correspondingly substituted phenoxybenzoic acid having the formula

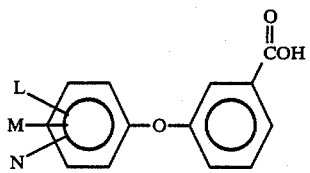

with about a stoichiometric amount of a diacylating agent having the formula HX—A'—X'H where A' is $R_5$,

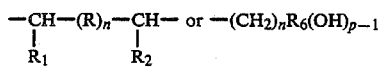

to produce the corresponding bis compound and then nitrating the bis compound to produce a compound having the formula

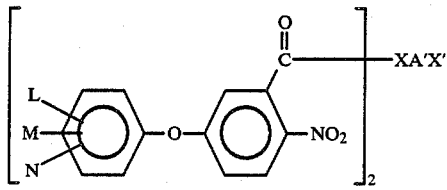

and then optionally transacylating the bis compound with an excess of said diacylating agent, preferably in the presence of a transacylating catalyst, to produce the compounds of formula 1 where A is I, III or V, namely

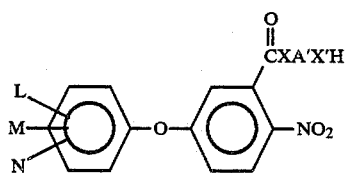

and further optionally reacting the product of transacylation where A' is $R_5$ with a carbonyl-containing compound of the formula

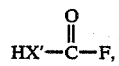

or the acid halide or anhydride of such carbonyl-containing compounds to produce the compounds of formula 1 where A is II or VI, namely

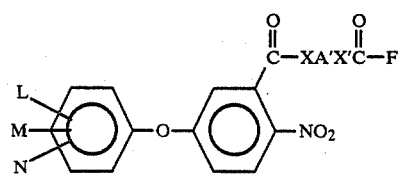

where F is $R_8$ or $(X'')_n R_6$.

2. The process for the preparation of substituted diphenyl ethers of claim 1 wherein A is group IV which comprises reacting a phenoxybenzoic acid having the formula

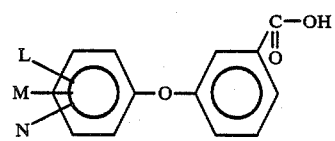

with a diacylating agent having the formula HX—A'—X'H wherein A' is $R_5$,

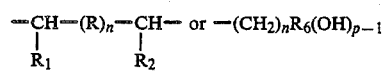

to produce the corresponding bis intermediate compound having the formula:

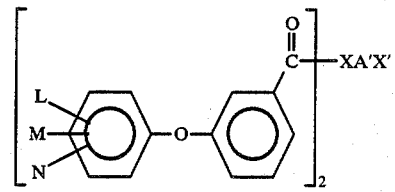

and then nitrating said bis compound with a nitrating agent to produce the product having the formula:

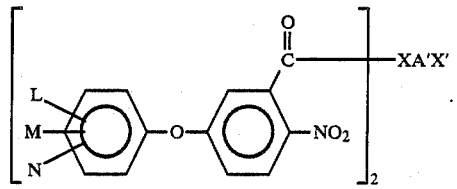

3. The process for the preparation of substituted diphenyl ethers of claim 1 wherein A is group I, III or V which comprises transacylating the product of claim 2 with an excess of said diacylating agent in the presence of a transacylating catalyst in a transacylation zone to produce the corresponding product having the formula:

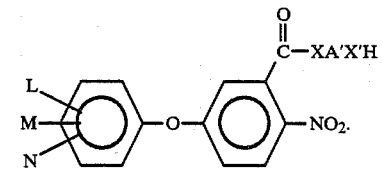

4. The process for the preparation of substituted diphenyl ethers of claim 1 wherein A group II or VI which comprises reacting the product of claim 3 where A' is $R_5$ with a carbonyl-containing compound selected from the group of a compound having the formula

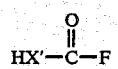

and the acid halide or anhydride of said compound wherein F is $R_8$ or $(X'')_nR_6$, to produce the product having the formula:

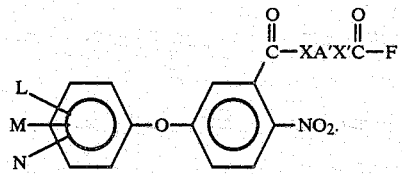

5. The process of claim 2 wherein the reaction of said phenoxybenzoic acid with said diacylating agent is effected at a temperature between about 20° and about 200° C. under from about 1 to about 5 atmospheres pressure and the nitration of said intermediate is effected at a temperature between about −5° and about 70° C. under atmospheric pressure.

6. The process of claim 5 wherein the nitration is effected in the presence of an inert solvent and the concentration of said intermediate compound in said solvent is between about 10 and about 30 weight percent.

7. The process of claim 5 wherein the mole ratio of said phenoxybenzoic acid to said diacylating agent is about 2:1 and the mole ratio of nitrating agent to said intermediate compound is about 2:1.

8. The process of claim 2 wherein said phenoxybenzoic acid is 3-(2-chloro-4-trifluoromethylphenoxy)benzoic acid.

9. The process of claim 8 wherein said diacylating agent is ethylene glycol.

10. The process of claim 8 wherein said diacylating agent is 1,3-propandiol.

11. The process of claim 8 wherein said diacylating agent is 2-hydroxyethyl ether.

12. The process of claim 8 wherein said diacylating agent is 2-hydroxyethyl sulfide.

13. The process of claim 3 wherein said transacylation reaction is effected at a temperature between about 20° and about 250° C. under from about 1 to about 5 atmospheres pressure.

14. The process of claim 13 wherein the catalyst is manganese acetate tetrahydrate.

15. The process of claim 13 wherein the catalyst is an acid.

16. The process of claim 13 wherein the mole ratio of diacylating agent to nitrated product is between about 1:1 and about 50:1 and unreacted diacylating agent is recycled to said transacylation zone.

17. The process of claim 13 wherein said diacylating agent is ethylene glycol.

18. The process of claim 17 wherein 1,2-bis[5-(2-chloro-4-trifluoromethylphenoxy)-2-nitrobenzoyloxy]ethane is reacted with ethylene glycol.

19. The process of claim 13 wherein 1,3-bis[5-(2-chloro-4-trifluoromethylphenoxy)-2-nitrobenzoyloxy]propane is reacted with 1,3-propanediol.

20. The process of claim 13 wherein 1,5-bis[5-(2-chloro-4-trifluoromethylphenoxy)-2-nitrobenzoyloxy]-3-oxapentane is reacted with 2-hydroxyethyl ether.

21. The process of claim 13 wherein 1,5-bis[5-(2-chloro-4-trifluoromethylphenoxy)-2-nitrobenzoyloxy]-3-thiapentane is reacted with 2-hydroxyethyl sulfide.

22. The process of claim 13 wherein 1,4-bis[5-(2-chloro-4-trifluoromethylphenoxy)-2-nitrobenzoyloxy]-2-butene is reacted with 1,4-butenediol.

23. The process of claim 4 wherein said reaction with said carbonyl-containing compound is effected at a temperature of between about 0° and about 200° C. under from about 1 to about 5 atmospheres pressure.

24. The process of claim 23 wherein the mole ratio of said carbonyl-containing compound to said transacylated component is between about 1:1 and about 20:1.

25. The process of claim 4 wherein 2-hydroxyethyl-5-(2-chloro-4-trifluoromethylphenoxy)-2-nitrobenzoate is reacted with a carbonyl-containing compound.

26. The process of claim 25 wherein the carbonyl-containing compound is acetic acid.

27. The process of claim 25 wherein the carbonyl-containing compound is chloroacetic acid.

28. The process of claim 25 wherein the carbonyl-containing compound is methoxyacetic acid.

29. The process of claim 25 wherein the carbonyl-containing compound is propionic acid.

* * * * *